United States Patent [19]
Teltscher

[11] 3,986,030
[45] Oct. 12, 1976

[54] EYE-MOTION OPERABLE KEYBOARD-ACCESSORY

[76] Inventor: Erwin S. Teltscher, 69 Diana's Trail, Roslyn, N.Y. 11576

[22] Filed: Nov. 3, 1975

[21] Appl. No.: 628,539

[52] U.S. Cl. .................................. 250/349; 197/98; 250/209; 250/215; 250/221; 340/365 P
[51] Int. Cl.² ................... B41J 5/08; G01D 21/04; G06M 7/00; G08C 1/00
[58] Field of Search .......... 250/221, 222, 208, 209, 250/518, 349, 215; 351/7; 197/98; 340/365 P

[56] References Cited
UNITED STATES PATENTS

| | | | |
|---|---|---|---|
| 3,064,552 | 11/1962 | Ehrsam, Jr. et al. | 250/271 X |
| 3,340,401 | 9/1967 | Young | 250/221 X |
| 3,379,885 | 4/1968 | Nork | 250/221 X |
| 3,507,988 | 4/1970 | Holmes | 351/7 X |
| 3,678,283 | 7/1972 | LaBaw | 250/216 |
| 3,806,725 | 4/1974 | Leitz | 250/221 X |

*Primary Examiner*—Alfred E. Smith
*Assistant Examiner*—T. N. Grigsby
*Attorney, Agent, or Firm*—Erwin S. Teltscher

[57] ABSTRACT

An eye-motion operable keyboard-accessory includes light source means for directing a light ray at an eye of an operator, for obtaining a light reflection therefrom, and a plurality of light-responsive sensors selectively actuable by the operator-reflected light ray. The sensors are connected to electrically operable key means disposed on a keyboard for actuation of the former upon the operator-reflected light ray striking one of the light-responsive sensors.

8 Claims, 4 Drawing Figures

U.S. Patent   Oct. 12, 1976   3,986,030
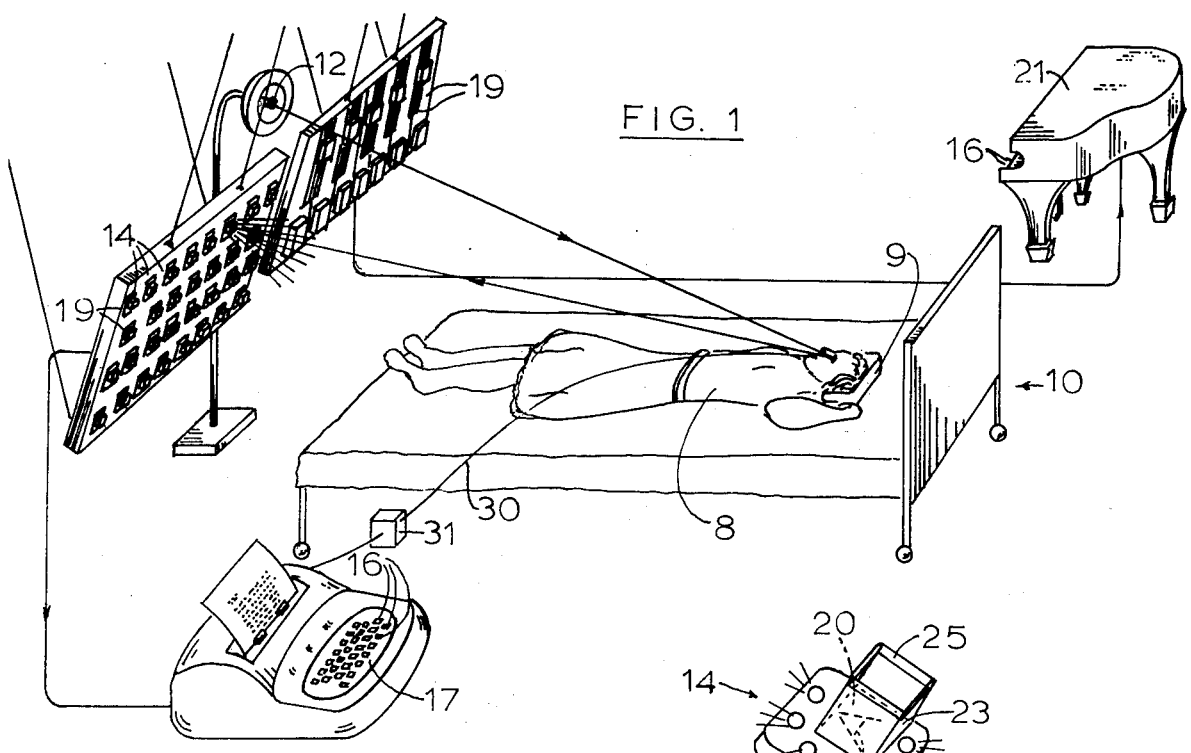
FIG. 1
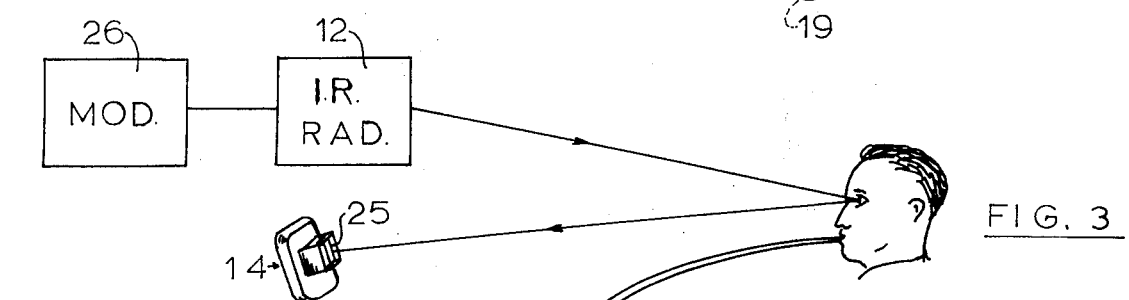
FIG. 2
FIG. 3
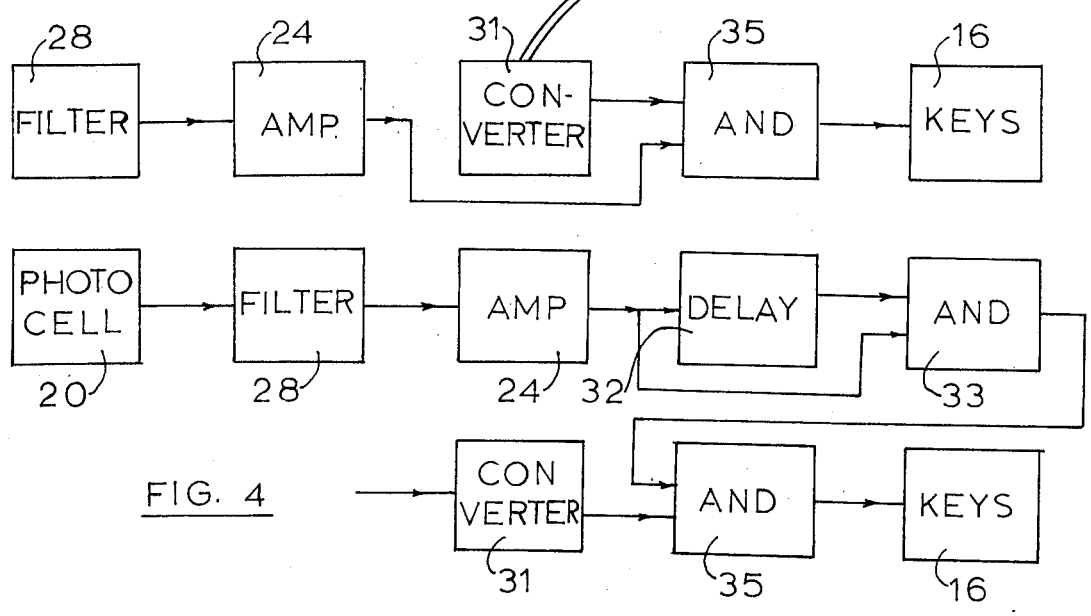
FIG. 4

EYE-MOTION OPERABLE KEYBOARD-ACCESSORY

BACKGROUND OF THE INVENTION

1. Field of the Invention.

The field of the invention relates to an eye-motion operable keyboard-accessory.

2. Description of the Prior Art.

The eye-motion operable keyboard-accessory is intended for paraplegics or persons whose arms and feet are otherwise fully occupied. Suction-operable keyboard accessories are known, where a paraplegic can operate a keyboard by means of coded suction impulses. Each of the coded suction impulses corresponds to a letter, and the operator must remember the code for each suction impulse corresponding to a respective letter and must successively actuate keys or the like on a keyboard. The operation of such a device is naturally very slow, and means have therefore been sought to increase its speed of operation.

SUMMARY OF THE INVENTION

It is therefore an object of my present invention to expedite the operating speed of a keyboard accessory suitable for operation by a paraplegic or the like.

It is another object of my invention that an operator need not remember any code, by means of which suction-pressure or the like is converted into a coded signal for actuation of a selected key.

I therefore provide an eye-motion operable keyboard-accessory which includes a light source for directing a light ray at an eye of an operator, and for obtaining a light reflection therefrom. A plurality of light-responsive sensors are arranged in a keyboard pattern. Each of the sensors has an output, and is selectively actuable by the operator-reflected light ray. The outputs of the sensors are connected to electrically actuable keys, respectively, and each of the keys is disposed on a keyboard; a key is selectively actuated by the operator-reflected light ray striking one of the light-responsive sensors. The keys include at least one mode-key for changing the operation thereof from a first mode to a second mode; and the light-source means is preferably an infra-red light source and the sensors are preferably infra-red light-responsive sensors. Infra-red to visible light-converter means are disposed on each of the sensors, respectively, for the illumination of the latter upon being struck by the operator-reflected light ray; an infra-red light passing filter is interposed between the operator and each of the light-responsive sensors. In one version of my invention, the light-converter means is an infra-red radiation sensitive phosphor. The keyboard-accessory additionally includes an index disposed on each of the light-responsive sensors which is representative of one of the keys, and which is targetable by the operator-reflected light ray. I further provide a light shield which is disposed between the index and the light-responsive sensor to shield the latter from light radiated by the phosphor.

In another version of my invention, the keyboard-accessory includes a light converter, consisting of an index disposed on each of the light-responsive sensors, and representative of one of the keys for being targetable by the operator-reflected light ray, a light-responsive photocell disposed in the vicinity of the index for converting light impinging thereon into electrical signals, illumination means disposed in the vicinity of the index for the illumination of the latter, a light shield placed between the index and the photo cell to shield the latter from light radiated by the illumination means, and triggering means connected to the light-responsive photocell and to the illumination means for switching a selected key on and off in dependence of the amount of infra-red light which impinges on the light-responsive photocell.

The infra-red light source includes modulation means for the modulation thereof with a tone. The light converter preferably includes filtering means which are interconnected between the light-responsive photocell and the triggering means for the switching of a selected key only in dependence of the tone-modulated infra-red radiation received by the light-responsive photocell.

Suction means are connected to the keys which are actuable by the operator for converting the presence and absence of suction pressure into electrical enabling and inhibiting signals, respectively. The keys are then actuable only in the presence of suction. The suction means include a pressure-to-electrical signal converter connected to the suction means and to the keys for converting the pressure to an electrical signal for switching the keys on and off.

In an alternate version of my invention, the keyboard accessory includes delay means interconnected between each of the light-responsive sensors and each of the electrically actuable keys, and a plurality of AND circuits. The inputs of each of the AND circuits are connected to the output of the delay means, and the output of each of the light-responsive sensors, respectively. The outputs of each of the AND circuits are connected to the keys, respectively, so that a selected key is actuated only in response to a preset dwell time of the operator-reflected light ray on one of the light-responsive sensors.

In one version of my invention the keyboard is a typewriter keyboard, and first and second sets of letters are printable by the keys in the first and second modes, respectively.

In another version of my invention, the keyboard is part of a musical instrument and the keys generate first and second sets of tones of different respective durations in the first and second modes.

BRIEF DESCRIPTION OF THE DRAWINGS

My invention will be better understood with reference to the accompanying drawing, in which:

FIG. 1 shows the general arrangement of the components of the system according to my invention;

FIG. 2 is a perspective view of the light-converter means;

FIG. 3 is a simplified block circuit diagram of the eye-motion operable keyboard-accessory; and FIG. 4 is a block circuit diagram of an alternate version of my invention.

DESCRIPTION OF THE PREFERRED EMBODIMENT

Referring now to the drawing, a severely handicapped person 8 such as for example, a paraplegic unable to move his arms and legs, has his head resting in a head support 9. The patient 8 is able to move the eye-motion operable keyboard-accessory 10 which includes a light source means 12 such as an infra-red radiation source, which emits light rays directed at the eye of the operator 8. The reflected light ray from an eye of the patient 8 strikes one of a plurality of light-responsive sensors 14 arranged in a keyboard pattern upon the patient 8 directing his eye to one of the sensors 14. The sensors 14 are connected to electrically actuable key means, respectively, disposed on a keyboard 17 for actuation of the key means upon the operator-reflected light ray striking one of the light-responsive sensors 14. The keyboard 17, may, for example, be the keyboard of an electric typewriter. At least one mode key 15 is included in the key means 16 for changing the operation of the latter from a first mode to a second mode; for example, the mode key means 15 may be the shift key of the conventional typewriter.

The light source is advantageously an infra-red light source, since the light rays emanating from such a source will not normally be visible to the patient; the sensors 14 are then infra-red light-responsive sensors. In order that the patient 8 may see whether his glance has been directed so as to strike a desired sensor, it is necessary to provide infra-red to visible light-converter means 18 disposed on each of the sensors 14, respectively, so that a selected sensor 14 may be illuminated and visible to the operation when it is struck by an operator-reflected light ray.

In one version of my invention, the light converter means is an infra-red radiation sensitive phosphor; an index 19 is disposed on each of the light-responsive sensors 14 and is representative of one of the key means for being targetable by the operator-reflected light ray; the index may have the form of numerals or letters. A light shield 23 is disposed between the index 19 and the light-responsive sensor 14 to shield the latter from light radiated by the phosphor.

In an alternate version of my invention, which requires only very low levels of illumination, I provide a light-responsive photocell 20 for converting light impinging thereon into electrical signals; each photocell 20 is disposed in the vicinity of the index 19. Illumination means 22 are disposed in the vicinity of the index 19 for the illumination of the latter, and a light shield 23 is disposed between the index 19 and a photocell 20 to shield the latter from light radiated by the illumination means 22.

Triggering means 24 in the form of, for example, an amplifier, are connected to the light-responsive photocell 20 and to the illumination means 22 for switching the illumination means 22 on and off in dependence of the amount of infra-red light impinging on the light responsive photocell 20. The illumination means 22 may, for example, be light bulbs.

It will be appreciated that visible light may erroneously actuate the photocell 20 and consequently result in a key 16 being erroneously struck. It is therefore advantageous if means are provided to distinguish visible light from infra-red light. This can, for example, be accomplished by an infra-red filter 25 interposed between the eye of the operator 8 and the light-responsive infra-red photocell 20.

An alternate method of differentiating the visible light from the infra-red light is to modulate the light source, and to provide an electrical filter beyond the photocell to pass only a modulated light striking the photocell. I accomplish this by providing a modulation means 26 for modulating the light source 12 with a tone. I then provide filtering means 28 for the light converter 18 which is interconnected between each light responsive photocell 12, and each triggering means 24, respectively, for switching the key means 16 only in dependence of the tone modulated infra-red radiation received by the light-responsive photocell 20. To insure that a key means 16 will not be inadvertantly operated when the eye of the operator 8 dwells unintentionally on a non-elected index 19, I provide suction means 30, connected to the key means 16 which are actuable by the operator 8 for converting the presence and absence of suction pressure into electrical enabling and inhibiting signals, respectively, so that the key means 16 are actuable only in the presence of such suction pressure. A pressure-to-electrical signal converter 31 is therefore connected to the suction means 30 and to the key means 16 for converting the suction pressure into an electrical signal to switch the key means 16 on and off.

The aforesaid implementation makes it possible for even an inexperienced operator to assure that only those of the keys 16 are struck which are intended to be operated by him.

A more experienced operator may be able to dispense with the suction means 30, if the apparatus, according to my invention, is so designed that a desired key 16 is only struck when the operator 8 dwells with his glance on one of the indices 19 for a minimum preselected time. For this optional mode of operation of the eye-motion operated keyboard-accessory, I provide a delay means 32 interconnected between each of the light-responsive sensors 14 and each of the electrically actuable key means 16.

I also provide a plurality of AND circuits 33; the inputs of each of the AND circuits 33 are connected to the output of delay means 32, and the output of each of the light-responsive sensors 14, respectively, and the outputs of each of the AND circuits 33 are connected to the key means 16, respectively, so that the latter are only actuable in response to a preset dwell time of the operator-reflected light ray on one of the light-responsive sensors 14.

Where the keyboard is a typewriter keyboard and includes, for example, a first set of lower case letters and a second set of upper case letters, these may be printable by the key means 16 in the first and second modes, respectively, upon actuation of the mode key means 15.

The keyboard 17 may alternately be the keyboard of a musical instrument 21 such as, for example, a piano, and the key means 16 then generate first and second sets of tone of different respective durations in the first and second modes; the loudness of the tones is dependent on the degree of the suction pressure.

Although the invention has been described with respect to a preferred form thereof, it is to be understood that it is not to be so limited since changes can be made therein which are within the full intended scope of this invention as defined by the appended claims.

What is claimed is:

1. An eye-motion operable keyboard-accessory comprising:
   invisible light-source means disposed in the vicinity and independent of the position of an operator for directing a light ray at an eye of the operator and obtaining a light reflection therefrom;
   a plurality of invisible-light responsive sensors arranged in a keyboard pattern, each of said sensors having an output and being selectively actuable by the operator-reflected light ray, the outputs of said sensors being connectible to a plurality of electrically actuable key means, respectively, for actuation of the key means upon said operator-reflected light ray striking one of said light-responsive sensors, and wherein the key means are disposed on a keyboard, and include at least one mode-key means for changing the operation of the key means from a first mode to a second mode;

a plurality of indices disposed in the vicinity of said invisible-light responsive sensors and representative of said key means, respectively, for being targetable by said operator-reflected light-ray; and limb-unaidedly operable confirming means connected to said key means for actuation of the latter only upon operation of said confirming means by the operator.

2. A keyboard accessory according to claim 1 further comprising:

a plurality of invisible to visible light-converter means disposed in the vicinity of said indices for illumination of the latter, respectively, upon being struck by said operator-reflected light ray;

a plurality of light shields disposed between said indices and said invisible-light responsive sensors for shielding the latter from the visible light generated by said light-converter means; and a plurality of invisible-light passing filters interposed between the operator and each of said light-responsive sensors.

3. A keyboard accessory according to claim 2 wherein said invisible-light responsive sensors are infrared light responsive sensors, said invisible light-source means are infrared light source means including modulation means for the modulation thereof with a tone, and said invisible-light to visible light converter means are infrared light to visible-light converter means including filtering means for passing only a tone-modulated infrared light ray generated by the modulated infrared light source means.

4. A keyboard accessory according to claim 1 wherein said confirming means are delay means having an input and an output, said delay means being interconnected between each of said light-responsive sensors and each of the electrically actuable key means, respectively, and a plurality of AND circuits, having two inputs and one output, the inputs of each of said AND circuits being connected to the output of said delay means, and the output of each of said light responsive sensors, respectively, the outputs of each of said AND circuits being connected to said key means, respectively, for actuation of the latter only in response to a preset dwell time of said operator-reflected light ray on one of said light-responsive sensors.

5. A keyboard accessory according to claim 1 wherein the keyboard is a typewriter keyboard, first and second sets of letters being printable by the key means in the first and second modes, respectively.

6. A keyboard accessory according to claim 1 wherein said confirming means are orally operable suction means connected to said key means and actuable by an operator for converting the presence and absence of suction pressure into electrical enabling and inhibiting signals, respectively, whereby said key means are actuable only in the presence of the suction pressure.

7. A keyboard accessory according to claim 6 wherein the suction means comprise a pressure-to-electrical signal converter connected to said suction means and to said key means for converting the pressure into an electrical signal for switching said key means on and off.

8. A keyboard accessory according to claim 6 wherein the keyboard is a keyboard of a musical instrument, and wherein said key means generate first and second sets of tones, of different respective durations in said first and second modes, and wherein the mode key means is a pedal and the loudness of said tones is dependent on the degree of said suction pressure.

* * * * *